United States Patent [19]
Yamamoto et al.

[11] Patent Number: 5,182,332
[45] Date of Patent: Jan. 26, 1993

[54] DENTAL COMPOSITION

[75] Inventors: Naoki Yamamoto; Nobuhiro Mukai; Hitoshi Ige; Junko Atarashi, all of Otake, Japan

[73] Assignee: Mitsubishi Rayon Co., Ltd., Tokyo, Japan

[21] Appl. No.: 561,178

[22] Filed: Aug. 1, 1990

[30] Foreign Application Priority Data

Aug. 2, 1989 [JP] Japan .................. 1-199487

[51] Int. Cl.⁵ .............. A61K 6/083; C08L 51/04; C08F 285/00
[52] U.S. Cl. .................. 525/305; 525/85; 525/304; 525/309; 525/310; 525/937; 522/120; 522/121; 522/149; 522/908; 523/115; 523/116
[58] Field of Search .......... 525/85, 304, 305, 309, 525/310, 937; 522/149, 908, 120, 121; 523/115, 116

[56] References Cited

U.S. PATENT DOCUMENTS

| | | | |
|---|---|---|---|
| 3,859,383 | 1/1975 | Tanno et al. | 260/876 R |
| 4,442,267 | 4/1984 | Charnock | 525/309 |
| 4,536,546 | 8/1985 | Briggs | 525/75 |
| 4,711,913 | 12/1987 | Tateosian | 523/115 |

FOREIGN PATENT DOCUMENTS

| | | |
|---|---|---|
| 0096527 | 12/1983 | European Pat. Off. . |
| 0158347 | 10/1985 | European Pat. Off. . |
| 2233031 | 1/1975 | France . |
| 8605793 | 10/1986 | PCT Int'l Appl. . |

*Primary Examiner*—David J. Buttner
*Attorney, Agent, or Firm*—Cushman, Darby & Cushman

[57] ABSTRACT

Disclosed is a dental composition comprising a (meth)acrylic ester compound as the principal component and containing a polymerization initiator, which is characterized by having incorporated therein a grafted rubber obtained by polymerizing at least one ethylenically unsaturated monomer in the presence of a rubber. This dental composition can be cured to yield a cured product having excellent strength properties and, therefore, is particularly useful in applications such as a molar restoration material and a denture base resin.

4 Claims, No Drawings

DENTAL COMPOSITION

BACKGROUND OF THE INVENTION a) Field of the Invention

This invention relates to dental compositions. More particularly, it relates to dental compositions which comprise conventional dental compositions having incorporated therein a polymer (grafted rubber) obtained by polymerizing at least one ethylenically unsaturated monomer in the presence of a rubber and which can yield cured products having excellent strength properties.

b) Description of the Prior Art

In the field of dental materials, conversion from metallic materials to polymeric materials is proceeding rapidly in recent years. Such dental materials include, for example, surface coating agents such as surface glazing agents and hard coating agents; composite resins such as filling composite resins, facing hard resins, composite resin inlays and jacket crowns; artificial teeth, denture bases and denture base liners; and orthodontic materials such as special impression tray materials and brackets.

Usually, these dental materials are composed chiefly of a (meth)acrylic ester compound and a polymerization initiator. Moreover, if need arises from the intended purpose, they can additionally contain inorganic materials, (meth)acrylic ester polymers, pigments, solvents, polymerization inhibitors, oxidation stabilizers and the like. Typically, they are cured by photopolymerization by means of visible light or ultraviolet radiation, by thermal polymerization, or by redox polymerization. Such cures are often performed in the mouth.

When such polymeric materials are regarded as dental substitute materials, they are more excellent in adhesion, appearance and workability than metallic materials. However, their mechanical properties such as strength have been still unsatisfactory.

With particular reference to molar composite resins which are materials for the restoration of molars, great importance is attached to their strength properties, because they are subject to high occlusal pressure characteristic of molars. In order to solve this problem, the concept of composite resin inlays has been proposed recently. This is based on the technique in which, outside the mouth, a composite resin is cured by two-stage polymerization (i.e., photopolymerization and thermal polymerization) to form an inlay having elevated cross-linking density and hence improved strength properties. However, several problems concerning pot life, workability and impact resistance remain to be solved.

Moreover, a composite denture base resin in which a siloxane polymer having a ladder structure is blended with PMMA in molecular order has also been proposed (Dental Materials and Equipment (in Japanese), 6, 4, 529, 1987). However, this is less than satisfactory.

In view of these circumstances, the present inventors made an intensive study and have found that, if a grafted rubber obtained by polymerizing at least one ethylenically unsaturated monomer in the presence of a rubber is incorporated in a conventional dental composition, there can be obtained a novel dental composition capable of yielding a cured product having excellent strength properties. The present invention has been completed on the basis of this finding.

SUMMARY OF THE INVENTION

It is an object of the present invention to provide a dental composition which can be cured to yield a cured product having excellent strength properties and which exhibits an outstanding effect especially when used as a molar restoration material subject to high occlusal pressure and as a denture base resin.

According to the present invention, there is provided a dental composition comprising a (meth)acrylic ester compound as the principal component and containing a polymerization initiator, which is characterized by having incorporated therein a grafted rubber obtained by polymerizing at least one ethylenically unsaturated monomer in the presence of a rubber.

DESCRIPTION OF THE PREFERRED EMBODIMENTS

The (meth)acrylic ester compound used as the principal component in the dental compositions of the present invention can be either a monofunctional compound or a polyfunctional compound which means a compound having one (meth)acrylic group and a compound having more than one (meth)acrylic group. Specific examples of monofunctional (meth)acrylic ester compounds include methyl (meth)acrylate, ethyl (meth)acrylate, propyl (meth)acrylate, butyl (meth)acrylate, hydroxyethyl (meth)acrylate, benzyl (meth)acrylate, methoxyethyl (meth)acrylate, glycidyl (meth)acrylate, tetrahydrofurfuryl (meth)acrylate, and methacryloyloxyethyltrimellitic mono ester and its anhydride.

Specific examples of polyfunctional (meth)acrylic ester compounds include di(meth)acrylates of ethylene glycol derivatives as represented by the general formula

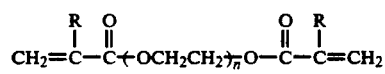

where R is hydrogen or methyl and n is a whole number of 1 to 20, such as ethylene glycol di(meth)acrylate, diethylene glycol di(meth)acrylate, triethylene glycol di(meth)acrylate, and polyethylene glycol di(meth)acrylate; 1,3-butanediol di(meth)acrylate, 1,4-butanediol di(meth)acrylate, 1,6-hexanediol di(meth)acrylate, glycerol di(meth)acrylate, bisphenol A di(meth)acrylate, bisphenol A diglycidyl di(meth)acrylate and ethoxylated bisphenol A diglycidyl di(meth)acrylate; urethane di(meth)acrylates; trimethylolpropane tri(meth)acrylate; tetrafunctional urethane tetra(meth)acrylates; pentaerythritol tetra(meth)acrylate, dipentaerythritol penta(meth)acrylate, and hexa(meth)acrylates of urethanes having an isocyanuric acid skeleton.

These (meth)acrylic ester compounds may be used alone or in admixture of two or more.

The (meth)acrylic ester compound used in the dental compositions preferably comprises at least one polyfunctional (meth)acrylic ester compound, and more preferably comprises (1) a polyfunctional (meth)acrylic ester compound and (2) at least one monofunctional (meth)acrylic ester compound and/or at least one polyfunctional (meth)acrylic ester compound other than the compound (1).

The polymerization initiator used in the dental compositions of the present invention may be suitably chosen according to the polymerization technique by which the dental composition is cured.

For thermal polymerization, various peroxides and azo compounds can be used. For photopolymerization by means of visible light or ultraviolet radiation, benzophenones, ketal compounds (such as benzoin dimethyl ether), benzoin alkyl ethers, anthraquinones, thioxanthones, acyl phosphine oxides and α-diketones can be used. Reducing agents such as tertiary amine compounds can also be used for purposes of photopolymerization. Moreover, redox polymerization can be performed by preparing the dental composition in two parts, one containing an oxidizing agent such as a peroxide and the other containing a reducing agent, and mixing them immediately before use. Such polymerization initiators are usually used in an amount of 0.1 to 5% by weight for thermal polymerization, 0.01 to 5% by weight for photopolymerization, or 0.1 to 10% by weight for redox polymerization.

If desired, the dental compositions of the present invention can additionally contain inorganic fillers (including silica powder, quartz powder and various glass powders such as barium glass powder) and (meth)acrylic ester polymers [such as polymethyl (meth)acrylate, polyethyl (meth)acrylate, and copolymers containing a (meth)acrylic ester as a principal component). Moreover, if desired, they can also contain pigments, solvents (such as ethanol and other alcohols, and ethyl acetate), polymerization inhibitors (such as hydroquinone, and 2,6-di-tert-butyl-4-methylphenol), oxidation stabilizers, ultraviolet light absorbers, pigments (such as titanium oxide and iron oxide), dyes and the like.

A characteristic feature of the dental compositions of the present invention is that, if a so-called grafted rubber, which is a polymer obtained by polymerizing at least one ethylenically unsaturated monomer in the presence of a rubber, is incorporated in a dental composition comprising a (meth)acrylic ester compound as the principal component and containing a polymerization initiator, there is obtained a novel dental composition capable of yielding a cured product having excellent strength properties.

The rubber constituting the grafted rubber can be an uncoated rubber consisting of a single rubber component, or a so-called multilayer composite rubber in which a core consisting of a non-rubber component or a different rubber component is coated with a layer of rubber or layers of rubber and non-rubber (so that the outermost layer is a layer of rubber).

Useful rubbers consisting of a single rubber component include, for example, diene rubbers such as polybutadiene, olefin rubbers such as EPDM, acrylate rubbers such as polybutyl acrylate, and siloxane rubbers. Useful multilayer composite rubbers include, for example, those obtained by polymerizing an acrylate monomer in the presence of a latex consisting of a hard resin (selected from polystyrene, styrene resins, AS resins and the like) or polybutadiene. Among these rubbers, acrylate rubbers and multilayer composite rubbers obtained by polymerizing an acrylate monomer in the presence of a core component are preferred. In such multilayer rubbers, the acrylate rubber is preferably present in an amount of 60 to 90% by weight and the core component preferably comprises polybutadiene.

As the ethylenically unsaturated monomer polymerized in the presence of a rubber to obtain a grafted rubber, there may be used one or more monomers, or a mixture of monomers, selected from the group consisting of (meth)acrylic ester compounds such as methyl (meth)acrylate and butyl (meth)acrylate; aromatic vinyl compounds such as styrene and α-methylstyrene; and vinyl cyanide compounds such as (meth)acrylonitrile. Even if the same acrylate monomer as used for the synthesis of the aforesaid rubber is used as the ethylenically unsaturated monomer, the resulting polymer is not an acrylate rubber but the soft component of the grafted rubber and, therefore, is not regarded as the "rubber" as used herein. On the other hand, if the rubber contains a non-rubber resin in its core or inner layer, this non-rubber resin functions as a part of the rubber and, therefore, is regarded as a component of the "rubber" as used herein.

In the above-described grafted rubber, the rubber component or components should preferably be in an amount of 10 to 90% by weight and more preferably 45 to 70% by weight.

Examples of the grafted rubber include those (comprising 45 to 70% by weight of rubber and 30 to 55% by weight of one or more ethylenically unsaturated monomers) obtained by polymerizing methyl methacrylate, or a combination of methyl methacrylate and acrylonitrile or styrene, in the presence of polybutyl acrylate rubber or a composite rubber which comprises a core consisting of polybutadiene, polystyrene or a copolymer of styrene or methyl methacrylate with butyl acrylate, and an outer layer consisting of an acrylate rubber composed principally of butyl acrylate or 2-ethylhexyl acrylate. More specifically, such grafted rubbers are commercially available under the trade names of Acryloid KM-330 (a product of Rohm and Haas Co., Ltd.), Kureha HIA-28 (a product of Kureha Chemicals Co., Ltd.), Kaneace FM (a product of Kanegafuchi Chemicals Co., Ltd.), Metabren W-800 (a product of Mitsubishi Rayon Co., Ltd.) and the like.

In the dental compositions of the present invention, the grafted rubber is preferably used in an amount of 0.01 to 10 parts by weight, more preferably 0.05 to 5 parts by weight, per 100 parts by weight of the (meth)acrylic ester compound. If the amount of grafted rubber used is less than 0.05 part by weight, the resulting composition will show little beneficial effect on its mechanical properties, while if it is greater than 10 parts by weight, the resulting composition will tend to show a reduction in mechanical properties.

The present invention is further illustrated by the following examples. However, it is to be understood that the present invention is not limited thereto. In these examples, all parts are by weight.

The procedure for the preparation of the grafted rubber (Acrylate C) used in some of the examples is described below.

(1) Preparation of a butadiene rubber latex (C-1)

A mixture composed of 100 parts of 1,3-butadiene, 4 parts of sodium laurate, 0.5 part of n-laurylmercaptan, 0.4 part of potassium persulfate and 180 parts of deionized water was charged into an autoclave which had been purged with nitrogen. This mixture was polymerized at 60° C. for 50 hours, with stirring, to obtain a rubber latex (having an average particle diameter of 0.09 μm). The degree of swelling was 25.

(2) Synthesis of a polymer latex for particle enlargement (D)

| | |
|---|---|
| Ethyl acrylate | 80 parts |
| Methacrylic acid | 20 parts |
| Potassium persulfate | 0.5 part |

| -continued | |
|---|---|
| Nonsaal TK-1 (a product of Nippon Fats and Oils Co., Ltd.; semisolid beef tallow potash soap) | 2.0 parts |
| Rapisol 80 (a product of Nippon Fats and Oils Co., Ltd.: sodium octylsulfosuccinate) | 1.0 part |
| Water | 200 parts |

A mixture prepared according to the above formulation was polymerized at 70° C. for 4 hours to obtain an emulsion latex having a pH of 6.2.

(3) Synthesis of an enlarged latex (C-2)

One hundred parts (on a solid basis) of the latex (C-1) was placed in a reaction vessel fitted with a stirrer. Then, 2.0 parts (on a solid basis) of the latex (D) was added thereto, with stirring, over a period of 10 seconds to obtain an enlarged latex (C-2). This enlarged latex had an average particle diameter of 0.5 μm.

(4) Preparation of an acrylate rubber

To 10 parts (on a solid basis) of the above enlarged latex (C-2) was added a mixture composed of 2 parts of Nonsaal TK-1 dissolved in 150 parts of deionized water, 189.5 parts of butyl acrylate and 0.5 part of triallyl cyanurate. The resulting mixture was heated to 50° C. and 0.2 part of potassium persulfate (dissolved in 10 parts of water) was added thereto. Then, the mixture was polymerized for 2 hours to obtain an acrylate rubber latex. The rate of polymerization of the butyl acrylate was not less than 99%.

(5) Preparation of a grafted rubber (Acrylate C)

To the total amount of the above acrylate rubber latex was added 0.6 part of Nonsaal TK-1 (dissolved in 10 parts of water). After the latex was heated to 80° C., 30 parts of styrene was added dropwise thereto at that temperature over a period of an hour, and the resulting mixture was held at that temperature for 2 hours. Then, 30 parts of methyl methacrylate was added dropwise thereto over a period of an hour, and the resulting mixture was held at that temperature for 2 hours to complete the polymerization. After being held at 80° C. for the specified time, the rates of polymerization of the styrene and the methyl methacrylate were not less than 99%. To the resulting latex was added 0.5 parts of a thermal stabilizer comprising an emulsion of B.H.T. (2,6-di-tert-butyl-p-cresol). Then, the latex was coagulated by pouring it into an aqueous solution of sulfuric acid. The precipitate so formed was washed with water, dehydrated and dried to obtain a graft copolymer in powder form.

EXAMPLE 1-7, COMPARATIVE EXAMPLE 1 AND REFERENCE EXAMPLES 1-3

Dental compositions I were prepared according to the formulation given below. Each of the dental compositions I was filled into a stainless steel mold, 4 mm in inner diameter and 6 mm in height, having a piece of 0.1 mm thick cover glass attached to the bottom thereof. After the top of the mold was covered with another piece of cover glass, the dental composition I was irradiated with light from a visible light irradiator (GC Light; manufactured by GC Dental Industries Co., Ltd.). The irradiation was performed for 60 minutes from each side of the mold to obtain a cured product for use in compression testing.

The cured products thus obtained were evaluated by measuring their compressive strengths with a Tensilon (IS-500; manufactured by Shimazu Seisakusho) at a crosshead speed of 1 mm/min. The results thus obtained are shown in Table 1.

| [Dental compositions I] | |
|---|---|
| 2,2-Bis[4-(3-methacryloyloxy-2-hydroxypropoxy)phenyl]propane (hereinafter referred to as Bis-GMA) | 0.8 part |
| Triethylene glycol dimethacrylate (hereinafter referred to as 3G) | 1.2 parts |
| Camphorquinone (hereinafter referred to as CQ) | 0.01 part |
| Dimethylaminoethyl methacrylate | 0.04 part |
| Grafted rubber | As shown in Table 1 |

TABLE 1

| | Grafted rubber | | |
|---|---|---|---|
| | Type | Amount used (wt. % based on monomers) | Compressive strength (kg/cm$^2$) |
| Example 1 | Acrylate c | 0.5 | 2,460 |
| Example 2 | Acryloid KM-330*[1] | " | 2,510 |
| Example 3 | Kureha HIA-28*[2] | " | 2,520 |
| Example 4 | Kaneace FM*[3] | " | 2,480 |
| Example 5 | Methabren W-800*[4] | " | 2,490 |
| Example 6 | Acrylate C | 0.01 | 2,330 |
| Example 7 | " | 10 | 2,270 |
| Comparative Example 1 | — | — | 2,000 |
| Reference Example 1 | Acrylate C | 0.005 | 1,980 |
| Reference Example 2 | " | 20 | 1,640 |

*[1] A product of Rohm & Haas Co., Ltd.; a polymer obtained by graft polymerization of MMA onto BA rubber.
*[2] A product of Kureha Chemicals Co., Ltd.; a polymer obtained by graft polymerization of AN/St/MMA onto Bd/St/2-ethylhexyl acrylate rubber.
*[3] B product of Kanegafuchi Chemicals Co., Ltd.; a polymer obtained by graft polymerization of MMA/AN onto BA rubber.
*[4] A product of Mitsubishi Rayon Co., Ltd.; a polymer obtained by graft polymerization of butyl acrylate/St/MMA onto butadiene rubber.

EXAMPLES 8-14, COMPRATIVE EXAMPLE 2 AND REFERENCE EXAMPLES 3-4

Cured products for use in compression testing were obtained in the same manner as in Example 1, except that the dental compositions II prepared according to the formulation given below were used. Then, their compressive strengths were evaluated in the same manner as in Example 1. The results thus obtained are shown in Table 2.

| [Dental compositions II] | |
|---|---|
| Ethoxylated bisphenol A dimethacrylate (hereinafter referred to as Bis-MEPP) | 1.2 parts |
| Isocyanuric acid-based urethane hexaacrylate having the structure given below (hereinafter referred to as U-6HA) | 0.4 part |
| 1,6-Hexanediol dimethacrylate (hereinafter referred to as 1,6-HD) | 0.08 part |
| Benzyl methacrylate (hereinafter referred to as BZ) | 0.32 part |
| CQ | 0.01 part |
| Isoamyl p-dimethylaminobenzoate (hereinafter referred to as DABA) | 0.04 part |

[Dental compositions II]

Grafted rubber      As shown in Table 2

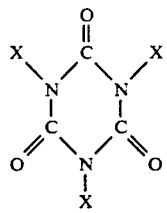

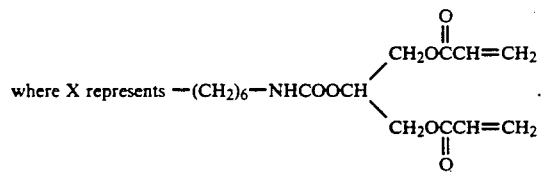

where X represents —(CH$_2$)$_6$—NHCOOCH

TABLE 2

| | Grafted rubber | | Compressive |
|---|---|---|---|
| | Type | Amount used (wt. % based on monomers) | strength (kg/cm$^2$) |
| Example 8 | Acrylate C | 0.5 | 2,480 |
| Example 9 | Acryloid KM-330 | " | 2,490 |
| Example 10 | Kureha HIA-28 | " | 2,540 |
| Example 11 | Kaneace FM | " | 2,460 |
| Example 12 | Methabren W-800 | " | 2,510 |
| Example 13 | Acrylate C | 0.01 | 2,310 |
| Example 14 | " | 10 | 2,290 |
| Comparative Example 2 | — | — | 1,980 |
| Reference Example 3 | Acrylate C | 0.005 | 1,960 |
| Reference Example 4 | " | 20 | 1,660 |

EXAMPLES 15-21, COMPARATIVE EXMPLE 3 AND REFERENCE EXAMPLES 5-6

Cured products were obtained in the same manner as in Example 1, except that the dental composition I was replaced by each of the dental compositions III prepared according to the formulation given below and that, instead of being photopolymerized, the dental composition III was redox polymerized by mixing solution A and B intimately, filling the resulting mixture immediately into the stainless steel mold used in Example 1, and allowing it to stand at room temperature for 10 minutes. Then, their compressive strengths were evaluated in the same manner as in Example 1. The results thus obtained are shown in Table 3.

[Dental compositions III]
(Solution A)

| Bis-GMA | 0.8 part |
|---|---|
| 3G | 1.2 parts |
| Benzoyl peroxide (hereinafter referred to as BPO) | 0.04 part |
| 2,6-Di-tert-butyl-4-methylphenol | 0.004 part |
| Grafted rubber | As shown in Table 3 |

[Dental compositions III]
(Solution B)

| Bis-GMA | 0.8 part |
|---|---|
| 3G | 1.2 parts |
| p-Tolyldiethanolamine | 0.04 part |
| Tetraethylthiuram disulfide | 0.004 part |

TABLE 3

| | Grafted rubber | | Compressive |
|---|---|---|---|
| | Type | Amount used (wt. % based on monomers)*[1] | strength (kg/cm$^2$) |
| Example 15 | Acrylate C | 0.5 | 2,410 |
| Example 16 | Acryloid KM-330 | " | 2,460 |
| Example 17 | Kureha HIA-28 | " | 2,470 |
| Example 18 | Kaneace FM | " | 2,430 |
| Example 19 | Methabren W-800 | " | 2,440 |
| Example 20 | Acrylate C | 0.01 | 2,280 |
| Example 21 | " | 10 | 2,220 |
| Comparative Example 3 | — | — | 1,950 |
| Reference Example 5 | Acrylate C | 0.005 | 1,930 |
| Reference Example 6 | " | 20 | 1,590 |

*[1] Based on the total amount of monomers present in the mixture of solutions A and B.

EXAMPLES 22-28, COMPARATIVE EXAMPLE 4 AND REFERENCE EXAMPELS 7-8

Cured products were obtained in the same manner as in Example 1, except that the dental composition I was replaced by each of the dental compositions IV prepared according to the formulation given below and that, instead of being photopolymerized, the dental composition IV was thermally polymerized by filling it into the stainless steel mold used in Example 1 and heating it at 60° C. for 5 hours. Then, their compressive strengths were evaluated in the same manner as in Example 1. The results thus obtained are shown in Table 4.

[Dental compositions IV]

| Urethane diacrylate having the structure given below | 1.2 parts |
|---|---|

-continued

[Dental compositions IV]

| | |
|---|---|
| 3G | 0.8 part |
| Finely powdered silica having an average particle diameter of 0.04 μm) | 2.0 parts |
| BPO | 0.04 part |
| Grafted rubber | As shown in Table 4 |

$$CH_2=\overset{CH_3}{\underset{O}{\overset{|}{C}}}CO(CH_2)_2OC\underset{O}{\overset{||}{N}}HCH_2\overset{CH_3}{\underset{CH_3}{\overset{|}{C}}}CH_2CH(CH_2)_2NH\underset{O}{\overset{||}{C}}O(CH_2)_2O\underset{O}{\overset{||}{\overset{CH_3}{\underset{|}{C}}}}C=CH_2$$

TABLE 4

| | Grafted rubber | | |
|---|---|---|---|
| | Type | Amount used (wt. % based on monomers) | Compressive strength (kg/cm²) |
| Example 22 | Acrylate C | 0.5 | 2,960 |
| Example 23 | Acryloid KM-330 | " | 3,010 |
| Example 24 | Kureha HIA-28 | " | 3,020 |
| Example 25 | Kaneace FM | " | 2,980 |
| Example 26 | Methabren W-800 | " | 2,990 |
| Example 27 | Acrylate C | 0.01 | 2,830 |
| Example 28 | " | 10 | 2,770 |
| Comparative Example 4 | — | — | 2,500 |
| Reference Example 7 | Acrylate C | 0.005 | 2,480 |
| Reference Example 8 | " | 20 | 2,140 |

EXAMPLES 29-35, COMPARATIVE EXAMPLE 5 AND REFERENCE EXAMPLES 9-10

Cured products for use in compression testing were obtained in the same manner as in Example 1, except that the dental compositions V (composite resins) prepared according to the formulation given below were subjected to photopolymerization. Then, their compressive strengths were evaluated in the same manner as in Example 1. The results thus obtained are shown in Table 5.

[Dental compositions V (composite resins)]

| | |
|---|---|
| Bis-MEPP | 1.2 parts |
| U-6HA | 0.4 part |
| 1,6-HD | 0.08 part |
| BZ | 0.32 part |
| CQ | 0.01 part |
| DABA | 0.04 part |
| Silane-treated quartz powder (quartz powder with an average particle diameter of 3 μm having 2% by weight of γ-methacryloyloxypropyl trimethoxy silane mixed therewith) | 8.0 parts |
| Grafted rubber | As shown in Table 5 |

TABLE 5

| | Grafted rubber | | |
|---|---|---|---|
| | Type | Amount used (wt. % based on monomers) | Compressive strength (kg/cm²) |
| Example 29 | Acrylate C | 0.5 | 3,480 |
| Example 30 | Acryloid KM-330 | " | 3,490 |
| Example 31 | Kureha HIA-28 | " | 3,540 |
| Example 32 | Kaneace FM | " | 3,460 |
| Example 33 | Methabren W-800 | " | 3,510 |
| Example 34 | Acrylate C | 0.01 | 3,310 |
| Example 35 | " | 10 | 3,290 |
| Comparative Example 5 | — | — | 2,980 |
| Reference Example 9 | Acrylate C | 0.005 | 2,960 |
| Reference Example 10 | " | 20 | 2,660 |

EXAMPLES 36-42, COMPARATIVE EXAMPLE 6 and REFERENCE EXAMPLES 11-12

Cured products were obtained in the same manner as in Example 1, except that the dental composition I was replaced by each of the dental compositions VI (denture base resins) prepared according to the formulation given below and that, instead of being photopolymerized, the dental composition VI was thermally polymerized by filling it into the stainless steel mold used in Example 1 and heating it at 60° C. for 5 hours. Then, their compressive strengths were evaluated in the same manner as in Example 1. The results thus obtained are shown in Table 6.

[Dental compositions VI (denture base resins)]

| | |
|---|---|
| Methyl methacrylate | 1.8 parts |
| Ethylene dimethacrylate | 0.2 part |
| BPO | 0.04 part |
| Polymethyl methacrylte (Acricon; a product of Mitsubishi Rayon Co., Ltd.) | 2.0 parts |
| Grafted rubber | As shown in Table 6 |

TABLE 6

| | Grafted rubber | | |
|---|---|---|---|
| | Type | Amount used (wt. % based on monomers) | Compressive strength (kg/cm²) |
| Example 36 | Acrylate C | 0.5 | 1,460 |
| Example 37 | Acryloid KM-330 | " | 1,510 |
| Example 38 | Kureha HIA-28 | " | 1,520 |
| Example 39 | Kaneace FM | " | 1,480 |
| Example 40 | Methabren W-800 | " | 1,490 |
| Example 41 | Acrylate C | 0.01 | 1,330 |
| Example 42 | " | 10 | 1,270 |
| Comparative Example 6 | — | — | 1,000 |
| Reference Example 11 | Acrylate C | 0.005 | 980 |
| Reference Example 12 | " | 20 | 640 |

What is claimed is:

1. A dental composition comprising a (meth)-acrylic ester compound as the principal component, wherein the (meth)acrylic ester compound contains at least one polyfunctional (meth)acrylic ester compound, and containing a polymerization initiator, which is characterized by having incorporated therein a grafted rubber obtained by polymerizing at least one ethylenically unsaturated monomer in the presence of a multilayer composite rubber obtained by polymerizing at least an acrylate monomer in the presence of a latex selected from the group consisting of styrene resins and polybutadiene and wherein the multilayer rubber contains 60 to 90 parts by weight of acrylate rubber and wherein the grafted rubber is present in an amount of 0.01 to 10 parts by weight per 100 parts by weight of the (meth)-acrylic ester compound.

2. A dental composition as claimed in claim 1 wherein the ethylenically unsaturated monomer is selected from the group consisting of (meth)acrylic ester compounds, aromatic vinyl compounds and vinyl cyanide compounds.

3. A dental composition as claimed in claim 1 wherein the grafted rubber is a multilayer composite rubber wherein the latex is polybutadiene and the grafted rubber is present in an amount of 0.05 to 5 parts by weight per 100 parts by weight of the (meth)-acrylic ester compound.

4. A dental composition as claimed in claim 1 which additionally contains an inorganic filler.

* * * * *